US007455985B2

(12) United States Patent
Stuart et al.

(10) Patent No.: US 7,455,985 B2
(45) Date of Patent: Nov. 25, 2008

(54) DETECTION AND QUANTIFICATION OF INTRACELLULAR PATHOGENS

(75) Inventors: Elizabeth S. Stuart, Amherst, MA (US); Lloyd H. Semprevivo, Wendell, MA (US)

(73) Assignee: University of Massachusetts, Boston, MA (US)

( * ) Notice: Subject to any disclaimer, the term of this patent is extended or adjusted under 35 U.S.C. 154(b) by 332 days.

(21) Appl. No.: 11/107,293

(22) Filed: Apr. 15, 2005

(65) Prior Publication Data

US 2006/0099661 A1    May 11, 2006

Related U.S. Application Data

(60) Provisional application No. 60/563,087, filed on Apr. 16, 2004.

(51) Int. Cl.
*G01N 33/571* (2006.01)
*G01N 33/53* (2006.01)
*G01N 33/00* (2006.01)
*G01N 33/48* (2006.01)
*G01N 33/533* (2006.01)

(52) U.S. Cl. ............... 435/7.36; 435/7.1; 435/7.24; 435/7.92; 435/40.51; 436/824; 436/800; 436/546

(58) Field of Classification Search .......... 435/7.36, 435/7.1, 7.24, 7.92, 40.51; 436/824, 800, 436/546
See application file for complete search history.

(56) References Cited

U.S. PATENT DOCUMENTS

| | | | |
|---|---|---|---|
| 5,656,271 A | 8/1997 | MacDonald et al. | 424/130.1 |
| 5,716,793 A | 2/1998 | MacDonald et al. | 435/7.36 |
| 5,840,297 A | 11/1998 | MacDonald et al. | 424/131.1 |
| 6,579,854 B1 | 6/2003 | Mitchell et al. | 514/31 |
| 2002/0001597 A1 | 1/2002 | Stuart et al. | |

FOREIGN PATENT DOCUMENTS

WO    WO 01/76628    10/2001

OTHER PUBLICATIONS

An et al., "Biochemical and Functional Antigenic Mimicry by a Polyclonal Anti-Idiotypic Antibody for *Chlamydia* Exoglycolipid Antigen", Pathobiology, vol. 65, pp. 229-240 (1998).
Apfalter et al., "Multicenter Comparison Trial of DNA Extraction Methods and PCR Assays for Detection of *Chlamydia pneumoniae* in Endarterectomy Specimens," J. Clin. Microbiol. vol. 39(2), pp. 519-524 (2001).
Balin et al., "Identification and Localization of *Chlamydia pneumoniae* in the Alzheimer's Brain," Med. Microbiol. Immunol. (Berl)., vol. 187(1), pp. 23-42 (1998).
Cascina et al., "Cutaneous Vasculitis and Reactive Arthritis Following Respiratory Infection Due to *Chlamydia pneumoniae*: Report of a Case," Clin. Exp. Rheumatol., vol. 20(6), pp. 845-847 (2002).
Hahn et al., "Serologic Markers for *Chlamydia pneumoniae* in Asthma," Ann. Allergy Asthma Immunol., vol. 84(2), pp. 227-233 (2000).
Haranaga et al., "Detection of *Chlamydia pneumoniae* Antigenin PBMNCs of Healthy Blood Donors," Transfusion, vol. 41(9), pp. 1114-1119 (2001).
Ikejima et al., "Removal of *Chlamydia pneumoniae* from Blood for Transfusion by Leukoreducation with Filters", Transfusion, vol. 42S, SP43, Special Abstract Supplement, 55th Annual Meeting, Orlando, FL, Oct. 26-29, 2002.
L'age-Stehr, J., "*Chlamydia pneumoniae* and Chronic Diseases" Proceedings of the State-of-the-Art Workshop held at Robert-Koch Institut Berlin Mar. 19 and Mar. 20, 1999.
Larson et al., *Chlamydia pneumoniae and Cardivascular Disease*, Med. J. Aust., vol. 177(10); pp. 558-562 (2002).
Levitt et al., "Binding, Ingestion, and Growth of *Chlamydia trachomatis* (L2 serovar) Analyzed by Flow Cytometry," Cytometry, vol. 7(4), pp. 378-383 (1986).
Mandy et al., Guidelines for the Performing Single-Platform Absolute CD4+ T-Cell Determinations with DC45 Gating for Persons Infected with Human Immunodefiency Virus; Jan. 2003/52 (RR02); 1-13, Morbidity & Morality Report (2003).
Peeling et al., "*Chlamydia pneumoniae* Serology: Interlaboratory Variation in Microimmunofluorescence Assay Results," J. Infect. Dis., vol. 181(Suppl 3):S426-9 (2000).
Peeling et al., "Standardization of *Chlamydia* serology: Improvement in Inter-laboratory Agreement of Micro-immunofluorescence Assay Results After a Workshop", J. Inf. Diseases, pp. 429-432 (2000).
Poccia et al., "Flow Cytometry and T-Cell Response Monitoring after Smallpox Vaccination", Emerging Infectious Diseases, Vo. 9(11), pp. 1468-1470 (2003).
Saikku, "Seroepidemiology in *Chlamydia pneumoniae*—atherosclerosis Association", Eur. Heart J., vol. 23(4), pp. 263-264 (2002).
Shi et al., "Assessment of Polymerase Chain Reaction and Serology for Detection of *Chlamydia pneumoniae* in Patients with Acute Respiratory Tract Infection", Chinese Medical Journal, pp. 184-187 (2002).
Sriram et al., "Multiple sclerosis associated with *Chlamydia pneumoniae* infection of the CNS", Neurology, vol. 50(2), pp. 571-572 (1998).
Stratton and Sriram, "Association of *Chlamydia pneumoniae* with Central Nervous System Disease," Microbes Infect. vol. 5(13), pp. 1249-1253 (2003).
Stuart et al., Chlamydial Glycolipid Antigen: Extracellular Accumulation in Biological Activity, and Antibody Recognition, Current Microbiology, vol. 28(2), pp. 85-90 (1994).
Tuuminen et al., "The Use of Serologic Tests for the Diagnosis of Chlamydial Infections," J. Microbiol. Methods, vol. 42(3), pp. 265-279 (2000).

(Continued)

*Primary Examiner*—S. Devi
(74) *Attorney, Agent, or Firm*—Fish & Richardson P.C.

(57) ABSTRACT

The present invention provides methods and compositions for detecting bacteria of the Chlamydiaceae family in a biological sample. Methods include, for example, contacting a biological sample with an antibody that specifically binds to a chlamydial antigen displayed on the surface of a *chlamydia*-infected blood cell; and analyzing the sample using fluorescence microscopy or flow cytometry to detect bound antibody.

11 Claims, 11 Drawing Sheets

OTHER PUBLICATIONS

Villareal et al., "Persistent Chlamydiae and Chronic Arthritis," Arthritis Res. vol. 4(1):5-94:5-9 (2001).

Von Hertzen, "Role of Persistent Infection in the Control and Severity of Asthma: Focus on *Chlamydia pneumoniae*," Eur. Respir. J., vol. 19(3), pp. 546-556 (2002).

Vora and Stuart, "A Role for the Glycolipid Exoantigen (GLXA) in Chlamydial Infectivity," Curr. Microbiol., vol. 46(3), pp. 217-223 (2003).

Waldman et al., "Flow Cytometric Analysis of *Chlamydia trachomatis* Interaction with L Cells," Cytometry, vol. 8(1), pp. 55-59 (1987).

Webley et al., "Cell Surface Display of the Chlamydial Glycolipid Exoantigen (GLXA) Demonstrated by Aantibody-dependent Complement-mediated Cytotoxicity," Curr. Microbiol., vol. 49(1), pp. 13-21 (2004).

Webley et al., "Successful Removal of *Chlamydophila pneumoniae* from Blood by Apheresis Leokoreduction," J. Clinical Apheresis, vol. 18(2), pp. 80-81 (2003), Abstract.

Whittum-Hudson et al., "The Anti-idiotypic Antibody to Chlamydial Glycolipid Exoantigen (GLXA) Protects Mice Against Genital Infection with a Human Biovar of *Chlamydia trachomatis*," Vaccine, vol. 19(28-29), pp. 4061-4071 (2001).

Wong et al. "Circulating *Chlamydia pneumoniae* DNA as a Predictor of Coronary Artery Disease," J. Am. Coll. Cardiol., vol. 34(5), pp. 1435-1439 (1999).

Fig. 1A Fig. 1B
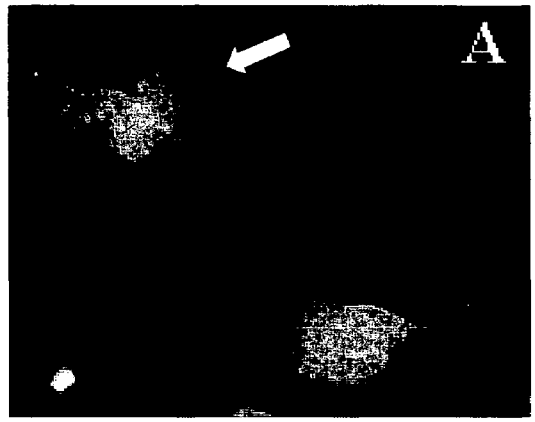 
 
Fig. 1C Fig. 1D

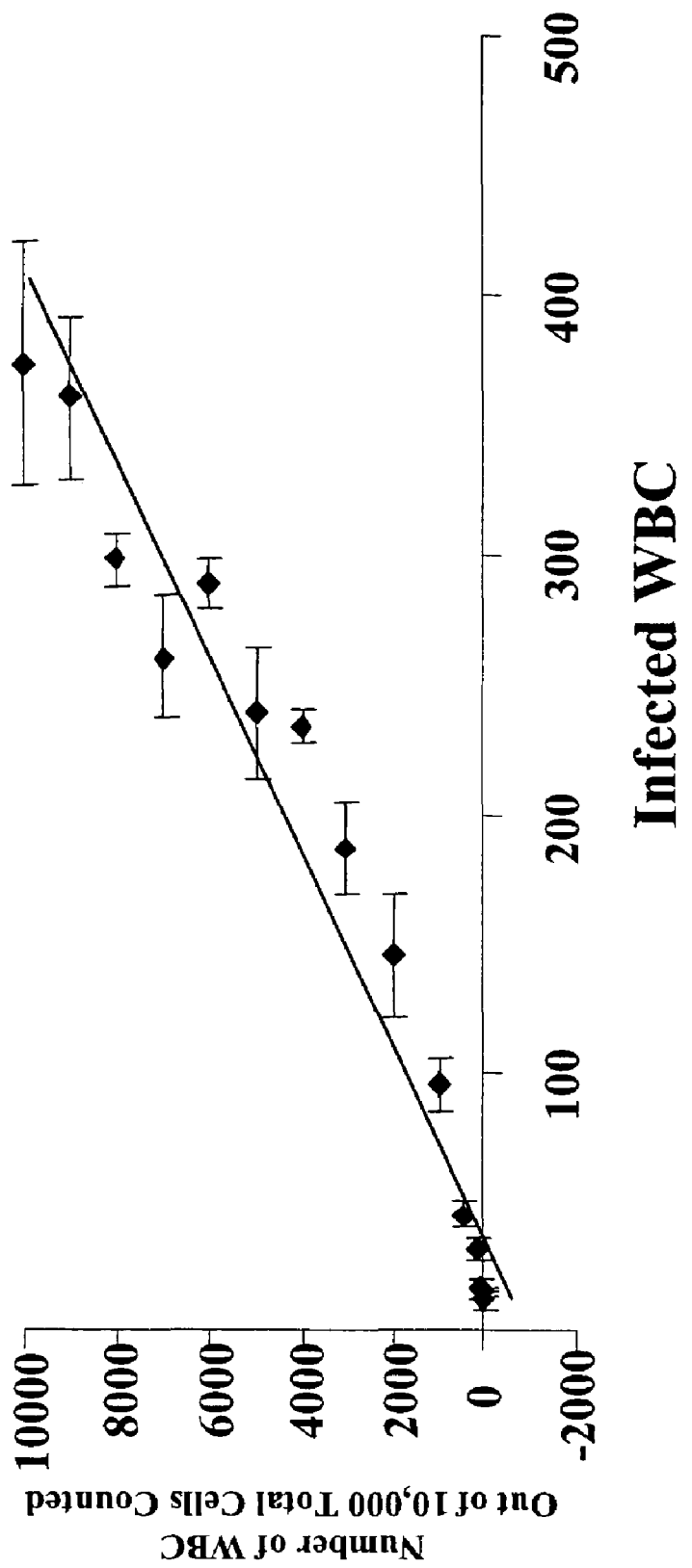

DETECTION AND QUANTIFICATION OF INTRACELLULAR PATHOGENS

CROSS-REFERENCE TO RELATED APPLICATIONS

This application claims priority to U.S. Provisional Application Ser. No. 60/563,087, filed on Apr. 16, 2004, the contents of which is incorporated herein by reference in its entirety.

TECHNICAL FIELD

This invention relates to methods and compositions for analyzing biological samples.

BACKGROUND

Infections by members of the Chlamydiaceae family constitute a growing public health problem. Two key pathogens for man are (1) *Chlamydia trachomatis,* agent of trachoma and sexually transmitted disease and (2) *Chlamydia pneumoniae,* agent of community acquired pneumonia and a leading pathogen candidate for initiation or exacerbation of chronic diseases. Such chronic diseases include, for example, atherosclerosis, cardiac artery disease, chronic obstructive pulmonary disease and neural pathologies such as multiple sclerosis and Alzheimer's disease.

The lack of methods to detect infectious as well as persistent *chlamydia* in patients is a public health problem. Simple identification and quantification methods are needed because these bacteria are "stealth" pathogens, frequently present, but not obviously in evidence. In addition, *chlamydia* cells were generally thought to occur infrequently if at all in blood, a routinely sampled biological fluid. As a result, tests to detect these pathogens are often not performed. Further, certain tests are invasive, often requiring biopsy followed by demonstration of the pathogen in tissue samples.

SUMMARY

The present invention is based, in part, on the discovery that *chlamydia* infects a wide range of white blood cell types and that these infections can be quantified. Surprisingly, even in subjects which appear asymptomatic for a chlamydial illness, the presence of *chlamydia* was found to be relatively common. Infected cells taken from subjects can be quantified by labeling the infected cells with antibodies that specifically bind to chlamydial antigens such as chlamydial glycolipid exoantigen (GLXA). Some of these antigens dissociate from the chlamydial bacterium itself and are expressed on the surface of or within, chlamydial host cells (e.g., white blood cells). Because chlamydial antigens can be expressed on the surface of or within infected blood cells, the actual number of such cells that is infected (e.g., monocytes, macrophages, B cells, T cells, basophils, mast cells, eosinophils, dendritic cells, or neutrophils) can be quantified in biological fluid samples (e.g., blood or urine) using flow cytometry. This technology permits quantification of infected cell load and, therefore, has significant value not only for diagnostic and quantification purposes, but also for tracking the efficacy of drug and vaccine treatments aimed at reducing or eliminating chlamydial infections. The present methods for analyzing a chlamydial infection have an advantage with respect to PCR methods in that the host cells that are actually infected are identified and not merely the presence of a chlamydial nucleic acid which can also be found outside of host cells. In addition, assessment of the number of *chlamydia* infected cells in a biological sample from a subject is a more accurate measure of the chlamydial load in a subject than is the number of copies of a chlamydial nucleic acid.

Accordingly, in one aspect, the invention provides methods for quantifying the number of *chlamydia* infected cells in a biological sample from a subject. The methods include contacting the biological sample that includes cells from a subject, with a first antibody that binds specifically to a chlamydial antigen present in or on the surface of a *Chlamydia*-infected cell and analyzing the biological sample using flow cytometry to detect cell bound first antibody. Detection of bound first antibody indicates that bacteria of the Chlamydiaceae family are present in the cell and the number of cells with bound first antibody is counted. The biological sample can be taken from individuals who are asymptomatic for a disorder caused by *Chlamydia*. A biological sample can be urine, blood, saliva, sputum, mucus, semen, amniotic fluid, synovial fluid, cerebrospinal fluid, mouth wash, bronchial lavage fluid, and any combination thereof. In some embodiments, a profile of a chlamydial infection can be determined in which the biological sample is also contacted with a second antibody that binds specifically to a cell type-specific antigen, e.g., an antigen that is expressed specifically in basophils, eosinophils (e.g., CDw125), neutrophils (e.g., CD 16b), dendritic cells, mast cells, or monocytes (e.g., CD 14). Cells which bind both the first and the second antibody are determined to be *chlamydia* infected cells of the cell type labeled by the second antibody. In some embodiments, the methods are applied to biological samples obtained from a subject at different time points, separated, e.g., by at least one week.

In another aspect, the invention provides methods for reducing the number of *chlamydia* infected cells in a biological sample obtained from a subject. The method involves contacting the biological sample from a subject with an anti chlamydial antigen antibody and using fluorescence activated cell sorting to separate the population of cells in the biological sample into a first subpopulation of cells with bound antibody that are considered to be infected and a second subpopulation of cells with a reduced number of *chlamydia* infected cells. In some embodiments the biological sample is a blood sample or a semen sample.

In any of the methods described herein, the chlamydial species that can be quantified include, e.g., chlamydial species selected from the group consisting of *Chlamydia trachomatis, Chlamydia suis, Chlamydia muridarum, Chlamydophila psittaci, Chlamydophila pneumoniae Chlamydophila caviae, Chlamydophila pecorum, Chlamydophila abortus,* and *Chlamydophila felis,* and any combination thereof. Antibodies used can be monoclonal, polyclonal, or a mixture of both monoclonal and polyclonal antibodies. For example, the antibody used can be an antibody that has the binding specificity of an antibody produced by the hybridoma deposited in the American Type Culture Collection (ATCC) as accession number ATCC H.B. 11300. Alternatively or in addition, fragments of antibodies may be used. Further, in any of the methods, the antibody (or fragment thereof) can be labeled with one or more fluorophores such as 7-amino-4-methylcoumarin-3-acetic acid (AMCA), TEXAS RED™, 5-(and-6)-carboxy-X-rhodamine, lissamine rhodamine B, 5-(and-6)-carboxyfluorescein, fluorescein-5-isothiocyanate (FITC), 7-diethylaminocoumarin-3carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5(and-6)-carboxamido]hexanoic acid, N-(4,4-difluoro-5,7-dimethyl-4-bora-3a,4a diaza-3-indacenepropionic acid, eosin-5-isothiocyanate, erythrosin-5- isothiocyanate, phycoerythrin (B-, R-, or cyanine-), allophycocyanin, OREGON GREEN™, and CASCADE™ blue acetylazide. Cell types that can be determined include, e.g., basophils, eosinophils, neutrophils, dendritic cells, mast cells, or monocytes. In any of the methods the chlamydial antigen can be e.g., chlamydial glycolipid exoantigen (GLXA).

The invention permits routine and highly sensitive quantitative assessment of chlamydial infections in subjects (e.g., humans, cattle, swine, goats, sheep, horses, dogs, cats, or poultry) and medically valuable biological fluids used for donations, e.g., blood, semen, and stem cells. In addition, the progression and cell type distribution of a chlamydial infection in a subject (e.g., a human patient) can be quantified over time and is thus very useful in assessing the efficacy of anti-chlamydial therapy in the subject. The invention can also be used to deplete *chlamydia* infected cells from samples of cells taken from a subject that are to be donated or used commercially (e.g., blood and sperm).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and from the claims.

DESCRIPTION OF DRAWINGS

FIGS. 1A-1D are microscope pictures illustrating indirect immunofluorescence staining of live *chlamydia*-infected and uninfected HeLa cells. FIG. 1A: Live *C. trachomatis* serovar K-infected HeLa cells were stained at 48 hours post-infection with mouse serum Ab3 and a fluorescein isothiocyanate (FITC)-conjugated secondary antibody and subsequently fixed in 1% paraformaldehyde. FIG 1B: Methanol-fixed *C. trachomatis* serovar K-infected HeLa cells stained with mouse serum Ab3. FIG 1C: HeLa cells that were co-incubated with *C. trachomatis*-derived GLXA for 2 hours prior to immunodetection with mouse serum Ab3. FIG 1D: HeLa cells that were coincubated with *C. trachomatis*-derived GLXA for 2 hours prior to immunodetection with mouse serum pre-bleed.

FIG. 2A: a weak positive result; FIG. 2B: a strong positive result; and FIG. 2C: an intermediate positive result. Cp negative=thick lines, Cp positive=thin lines with arrows.

FIGS. 3A and 3B are *chlamydia*-positive smears, in which infected cells exhibit characteristic chlamydial inclusions that are immuno-stained with a FITC-conjugated secondary antibody. FIG. 3C shows a *chlamydia* negative immuno-smear.

FIG. 4A shows peripheral blood cells infected with *chlamydia* and co-cultured with J774A.1 host cells. FIG. 4B shows uninfected peripheral blood cells co-cultured with J774A.1 host cells.

FIG. 11 is a graph showing the detection, by flow cytometry, of *chlamydia* infected white blood cells that are serially diluted with red blood cells. As a test of the sensitivity of the method, *chlamydia* infected white blood cells were serially diluted with red blood cells, to obtain a total population of 50,000 cells. For flow cytometry analysis, a 10,000 cell sample was used. The vertical axis indicates the total number of white blood cells in the sample used for flow cytometry (e.g., 50% white blood cells in the counted sample corresponds to 5,000 cells on the vertical axis). The horizontal axis indicates the number of infected cells detected in the 10,000 cell sample counted by flow cytometry.

DETAILED DESCRIPTION

Figure 2A:
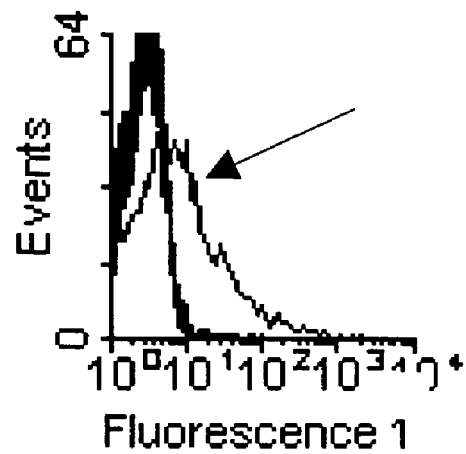
FIGS. 2A-2C are graphs illustrating results obtained from flow cytometry studies of buffy coats (mixtures of primarily white blood cells) from *Chlamydophila pneumoniae* (Cp) positive blood samples.

The invention provides novel, minimally invasive methods for detecting and/orquantifying *chlamydia* infected cells in any type of biological sample. The methods involve exposing a biological sample to an anti-chlamydial antibody (e.g. an anti-GLXA antibody) or fragment thereof and analyzing the biological sample using flow cytometry, or any variation thereof. The methods described herein can be performed in an automated system, e.g., a high-throughput system, for analyzing many biological samples at the same time.

The methods can, for example, enable medical practitioners to diagnose whether a patient (a) is or is not currently infected with bacteria of the Chlamydiaceae family; and (b) if the patient is infected, the patient's infection status. In determining a patient's infection status, a determination is made as to how many bacteria a patient carries (i.e., a patient's "chlamydial load"). If a patient carries a relatively high chlamydial load, the patient may be a symptomatic carrier of the bacteria (i.e., the patient may exhibit outward signs of the disease). If the patient carries a relatively low chlamydial load, the patient may have recently been infected or may be an asymptomatic carrier of *chlamydia*. The methods are particularly useful for diagnosing patients as being carriers of *chlamydia*, i.e., as persistently carrying a chlamydial load high enough to allow transmission to others but low enough that the patient does not display disease symptoms. Where a patient has undergone, is undergoing, or will undergo a therapeutic treatment to reduce/eliminate *chlamydia* from a patient, the methods are particularly useful for monitoring the effectiveness of the therapeutic treatment over time.

For example, the chlamydial load can be determined at a point in time prior to the beginning of a therapeutic treatment to eliminate the chlamydial infection and at various time points thereafter. The relative distribution of *chlamydia* in various cell types can also be determined (i.e., the profile of the chlamydial infection), e.g., the number of infected eosinophils, neutrophils, basophils, mast cells, and monocytes or any combination thereof that could be useful in determining the status of the chlamydial infection in a subject at various points in time. The methods can also be used to remove *chlamydia* infected cells from a fluid biological sample taken from a subject, e.g. by labeling cells that are *chlamydia* infected with an antibody that binds specifically to a chlamydial antigen and using fluorescence activated cell sorting (FACS) to remove the labeled cells from the biological sample.

In other embodiments, a level of *chlamydia* infected cells, e.g., of a specific type (e.g., basophils, eosinophils, neutrophils, dendritic cells, monocytes, or mast cells), is analyzed as a routine blood test that is done once, twice, or more per year. The test can be done starting with infants, and then continued on an annual basis through childhood and into adulthood. A profile of this level can then be established for classes of patients, e.g., by age, race, sex, or geography, or for the specific patient, and used for future diagnostic purposed. For example, if a patient has a specific level of infected cells when he or she is asymptomatic (e.g., a basal level), which may remain essentially the same over time (with potential increases and decreases based on the time of year, e.g., somewhat higher in the winter months), then a rise, e.g., a sudden or otherwise unusual rise, in this basal level, can indicate the onset of disease symptoms induced by *chlamydia*. The same type of test can also be done, e.g., in livestock, poultry, or horses, particularly in animals that are used for breeding.

In other embodiments, *chlamydia* infected cells can be depleted from a medically or commercially valuable biological fluid, e.g., blood, semen, stem cells, using an anti-chlamydial antigen antibody to label live infected cells. In one embodiment, depletion of *chlamydia* infected cells is done prior to storage or banking of the depleted population of cells for storage and future use (e.g., frozen sperm).

I. Production of Antibodies

Antibodies directed against certain chlamydial antigens can be used to carry out the methods of the present invention. In one embodiment, anti-GLXA antibodies are used. In another embodiment, anti-chlamydial antibodies, e.g., commercially available polyclonal antibodies such as guinea pig anti-*chlamydia* (available, e.g., from BioMedia) are used.

Monoclonal or polyclonal antibodies having specific binding affinity for chlamydial antigens (from, e.g., *Chlamydia trachomatis, Chlamydia suis, Chlamydia muridarum, Chlamydophila psittaci, Chlamydophila pneumoniae Chlamydophila caviae, Chlamydophila pecorum, Chlamydophila abortus*, and/or *Chlamydophila felis*), such as the GLXA epitope, can be produced using standard methods. Exemplary methods and antibodies useful in the present invention are described in U.S. Pat. Nos. 5,716,793 and 5,840, 297, which are both incorporated herein by reference in their entirety. For example, monoclonal antibodies obtainable from the hybridomas deposited in the American Type Culture Collection (ATCC) as accession numbers ATCC H.B. 11300 and 11301 can be used.

As used herein, the terms "antibody" or "antibodies" include intact antibody molecules and fragments thereof that are capable of binding to a chlamydial antigen such as GLXA. The term "epitope" refers to an antigenic determinant on an antigen to which the paratope of an antibody binds. Epitopic determinants typically consist of chemically active surface groupings of molecules such as amino acids or sugar side chains, and typically have specific three dimensional structural characteristics, as well as specific charge characteristics. Epitopes generally have at least five contiguous amino acids. The terms "antibody" and "antibodies" include, e.g., polyclonal antibodies, monoclonal antibodies, humanized or chimeric antibodies, single chain Fv antibody fragments, Fab fragments, and F(ab)$_2$ fragments. Antibodies used in the present invention can be of any immunoglobulin class, e.g., IgG, IgM, IgE, IgA, IgD, and any subclass thereof.

Chimeric antibodies are also useful in the present invention. A chimeric antibody is a molecule in which different portions are derived from different animal species, such as those having a variable region derived from a murine monoclonal antibody and a human immunoglobulin constant region. Chimeric antibodies can be produced through standard techniques.

Antibody fragments that have specific binding affinity for a chlamydial antigen, e.g., GLXA, can be generated by known techniques. Such fragments include, but are not limited to, F(ab')$_2$ fragments that can be produced by pepsin digestion of the antibody molecule, and Fab fragments that can be generated by reducing the disulfide bridges of F(ab')$_2$ fragments. Alternatively or in addition, Fab expression libraries can be constructed. See, for example, Huse et al., 1989, Science, 246:1275.

Alternatively or in addition, single chain Fv antibody fragments can be used. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques. See, for example, U.S. Pat. No. 4,946,778.

Once obtained or produced, antibodies or fragments thereof can be tested for recognition of chlamydial antigens by standard inmunoassay methods including, for example, Enzyme-linked Immunosorbent Assay (ELISA) techniques and radioimmunoassays (RIA). See, e.g., Short Protocols in Molecular Biology, Chapter 11, Green Publishing Associates and John Wiley & Sons, Edited by Ausubel, F.M et al., 1992. Suitable antibodies may have equal binding affinities for recombinant and native proteins.

II. Labeled Antibodies

Antibodies useful in the present invention can be labeled with a fluorophore that emits light of a particular color, e.g., a color that contrasts with other fluorophores. Alternatively or in addition, labeled secondary antibodies directed against the anti-chlamydial antibodies can be used. Labeled antibodies can be purchased or produced for use in the present invention. Techniques for labeling antibodies are well known in the art, and are described, for example, in Harlow et al., Antibodies: A Laboratory Manual, Cold Spring Harbor Laboratory, Cold Spring Harbor, N.Y., 353-355 (1988). For example, a skilled practitioner may choose to label antibodies with one or more of the following fluorophores: 7-amino-4-methylcoumarin-3-acetic acid (AMCA), TEXAS RED™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocycnate, 5-(and-6)-carboxytetramethylrhodamine, 7-hydroxycoumarin-3-carboxylic acid, 6-[fluorescein 5(and-6)-carboxamido]hexanoic acid, N-(4,4-difluoro-5,7-dimethyl-4-3a,4a diaza-3-indacenepropionic acid, eosin-5-isothiocyanate, erythrosin-5-isothiocyanate, phycoerythrin (B-, R-, or cyanine-), allophycocyanin, OREGON GREEN™, and/or CASCADE™ blue acetylazide (Molecular Probes, Inc., Eugene, Oreg.). Antibodies can also be labeled with electrochemical labels (Bio Veris).

Alternatively or in addition, antibodies can be labeled with semiconductor nanocrystals. Water soluble nanocrystals are composed of different sizes of cadmium-selenium/cadmium-sulfur core-shell nanocrystals enclosed in a silica shell or cadmium-selenium/zincsulfur nanocrystals solubilized in mercaptoacetic acid. Such water soluble nanocrystals have a narrow, tunable, symmetric emission spectrum and are photometrically stable. See e.g., Bruchez Jr. et al., Science, 1998, 281:2013-2016; and Chan et al., Science, 1998, 281:2016-2018, both of which are incorporated herein by reference in their entirety.

III. Samples for Analysis

The methods described herein can be used to analyze biological samples obtained from a subject. The term "subject" is used throughout the specification to describe an animal or human from which a biological sample may be obtained. The subject can be asymptomatic, or appear to be healthy, as we have found that a subject may be infected with *chlamydia*, and have a basal level of *chlamydia* infected cells, but have no symptoms of a *chlamydia*-induced disease, e.g., pneumonia, blinding trachoma, pelvic inflammatory disease, or sexually acquired reactive arthritis. Veterinary applications are clearly contemplated by the present invention. The term animal includes, but is not limited to, birds, reptiles, amphibians, and mammals, e.g., primates, pigs, rodents such as mice and rats, rabbits, guinea pigs, hamsters, cows, horses, cats, dogs, sheep, and goats. The term "biological sample" refers to material obtained from a patient that can be analyzed using fluorescence microscopy and/or flow cytometry. The biological sample can, for example, be any fluid obtainable from a patient, e.g., urine, blood, saliva, sputum, mucus, semen, amniotic fluid, mouth wash, bronchial lavage fluid, synovial fluid, cerebrospinal fluid, peritoneal washes, urine, and/or umbilical cord blood. A sample for analysis may be obtained from a patient using any method known to those of skill in the art.

IV. Analysis

Typically, biological samples are prepared for analysis by fluorescence microscopy and/or flow cytometry using art-known methods. However, as part of the preparation, the biological samples are contacted with anti-chlamydial antibodies, e.g., anti-GLXA antibodies. In addition, cells can also be contacted with a second antibody that recognizes a differentiating antigen, such as a cell-type specific marker (e.g., CD14, CD 16b, or CDw125). Binding of each primary antibody can be distinguished using any means known to those of skill in the art, e.g., by using distinctly labeled secondary antibodies to detect them. A secondary antibody can be used, e.g., to identify subpopulations of cells with specific characteristics identified with the presence of the differentiating antigen (e.g., eosinophils are identified by the presence of CD14 on monocytes). The differentiating antigen can be present on the surface of a cell or inside a cell. In one example, a sample of white blood cells that contains chlamdyia infected cells can be analyzed for the relative fraction of different white blood cell types. Thus, a given cell can be simultaneously assayed by flow cytometry for the presence of a chlamydial antigen and the presence of a white blood cell type-specific marker.

Methods for preparing samples for analysis, performing fluorescence microscopy to detect *chlamydia*-infected cells, and performing flow cytometry, are well known in the art and are described, for example, in Norkin et al., Exp. Cell. Res. 266(2):229-38 (2001); Handbook of Flow Cytometry Methods. J. Paul Robinson (Editor) Wiley (1993); and Guide To Flow Cytometry Methods W.McLean, Grogan James, M. Collins. Marcel Dekker, Inc, New York, (1990); Poccia et al, Emerging Infectious Diseases, 9 (11) 03-0349 (2003); and Mandy et al., Guidelines for the Performing Single-Platform Absolute CD4+ T-Cell Determinations with CD45 Gating for Persons Infected with Human Immunodeficiency Virus; January 2003/52 (RR02); 1-13. Morbidity & Mortality Report.

In flow cytometry, a sample containing cells (or cellular fragments) labeled or conjugated with a fluorescent dye is typically passed through a slender flow cell along with a sheath fluid so that the cells flow in single file. The individual cells in the flow are irradiated one at a time with a light beam (such as a laser beam) by means of hydrodynamic focusing, and the intensity of scattered light or fluorescent light from the cells, e.g., light information indicative of the cells, is measured instantaneously to analyze the cells. Flow cytometry of this kind is advantageous in that a large number of cells can be analyzed at high speed and with great accuracy.

Flow cytometers are well known in the art and are commercially available from, e.g., Beckman Coulter and Becton, Dickinson, and Company. Typical flow cytometers include a light source, collection optics, electronics and a computer to translate signals to data. In many cytometers, the light source of choice is a laser which emits coherent light at a specified wavelength. Scattered and emitted fluorescent light is collected by two lenses (one set in front of the light source and one set at right angles) and by a series of optics, beam splitters and filters, specific bands of fluorescence can be measured.

One known example of a cell analyzing apparatus using flow cytometry comprises a flow cell for forming a slender stream of liquid, a light source (such as a laser) for irradiating the cells which flow through the interior of the flow cell with a light beam, a photodetector for detecting cell light information from the cells irradiated with the light beam and converting the light information into an electric signal, a signal processing circuit for amplifying, integrating, and removing noise from the signal produced by the photodetector, and a computer for processing a signal, which represents the cell light information, outputted by the signal processing circuit. In addition to analysis, flow cytometry can be used to sort cells found in a biological sample into physically separated populations a process known as fluorescence activated cell sorting (FACS), which is particularly useful in removing *chlamydia* infected cells that have been labeled with an anti-chlamydial antigen antibody from a biological sample obtained from a subject.

Skilled practitioners will appreciate that many variations and/or additions to basic flow cytometry systems can be made, e.g., providing practitioners with additional and/or different analyzing capabilities. Further, skilled practitioners will appreciate that flow cytometry can be performed in an automated manner and that a flow cytometer can be provided as part of a larger, automated system, e.g., a high-throughput system. The methods of the present invention contemplate the use of such apparatus and systems. Also included within the present invention is the use of any apparatus not known as a flow cytometer (e.g., a fluorescence activated cell sorter), but which performs essentially the same function as a flow cytometer.

In some cases, it may be desirable to determine the subcellular localization of chlamydial antigens. Confocal fluorescence microscopy can be used to precisely determine the location of anti-chlamydial immunofluorescence staining within a cell. Confocal imaging allows detection of fluorescence within a very thin plane (optical section) through the imaged cell. By taking a series of confocal optical sections through the entire depth of a cell (i.e., from top to bottom) it is thus possible to localize chlamydial antigens with high subcellular spatial resolution (for a recent review on confocal microscopy see Miyashita, Methods Mol. Biol., 261:399-410 (2004)).

EXAMPLES

Example 1

*Chlamdophila pneumoniae* in Random Blood Samples from Different Age Groupings: Flow Cytometric and Blood Smear Analysis

*Chlamydophila pneumoniae* (Cp) is an obligate intracellular pathogen associated with outbreaks of community acquired pneumonia. Cp can infect numerous cells, including B and T cells, and its putative involvement in cardiovascular disease, asthma, senile dementia, and autoimmune disorders, make it of increasing interest. Findings from standard Cp culture with HEp-2 implied Cp was fastidious, so molecular techniques and not in vitro culture have become a norm. A pilot survey of 500 normal blood donors examined Cp positivity by immunostaining peripheral blood smears and in vitro culture of buffy coat (BC) cells. Their agreement was excellent: 25%±1.6% and 24%±1.2% and demonstrated the viability and infectivity of Cp in these samples. Flow cytometry (FC) is an alternative, clinically relevant *Chlamydia*-detection method and one that permits quantification of pathogen load and identification of cell type specific pathogen burden (i.e., an identification of which types of cells harbor the pathogen).

Methods: EDTA blood samples collected from patients at a health clinic were titered for anti-Cp antibody by ELISA and a Cp specific peptide. BC smear preparations were immunostained and BC lysates tested in vitro by culture on the mouse macrophage (J774A.1) monolayers for 96 h, at which time they were immunostained, examined and scored. The remaining BC was washed, fixed, permeabilized, stained and analyzed by FC for Cp containing cells.

Results: Initial results indicate the FC technique readily detected Cp infected peripheral blood cells (PBC). The difference in mean fluorescence intensity of infected versus uninfected cells within a given sample was as high as 110-fold and infected cells were characterized by a higher side scatter. FC statistical data also indicated that of the 10,000 events counted in Cp positive samples, there were 1174±388 infected cells. Finally, there was a positive correlation between the number of infected cells seen on smear and in culture and the quantity of infected cells detected by FC analysis. Typical blood smear and flow cytometry results are provided in FIGS. 1A-1D, 2A-2C, and, 3A-3C, respectively.

FIG. 1A is a picture of live *C. trachomatis* serovar K-infected HeLa cells stained at 48 hours post-infection with mouse serum Ab3 and a FITC-conjugated secondary antibody and subsequently fixed in 1% paraformaldehyde. Note that the live infected cells fluoresce (arrow). FIG. 1B is a picture of methanol-fixed *C. trachomatis* serovar K-infected HeLa cells stained with mouse serum Ab3. Note in FIG. 1B that the use of methanol for fixation removed GLXA from cell surface. FIG. 1C is a picture of viable uninfected HeLa cells co-incubated for 2 hours with *C. trachomatis*-derived GLXA prior to immunodetection with mouse serum Ab3. FIG. 1D is a picture of viable uninfected HeLa cells co-incubated for 2 hours with *C. trachomatis*-derived GLXA prior to immunodetection with a mouse serum pre-bleed. Note that the speckled staining pattern in FIG. 1C is restricted to the HeLa cell surface and can only be visualized in the presence of anti- GLXA antibody. The results presented in FIGS 1A-1D are representative of three experiments. Original magnification: X400.

Figure 2B:
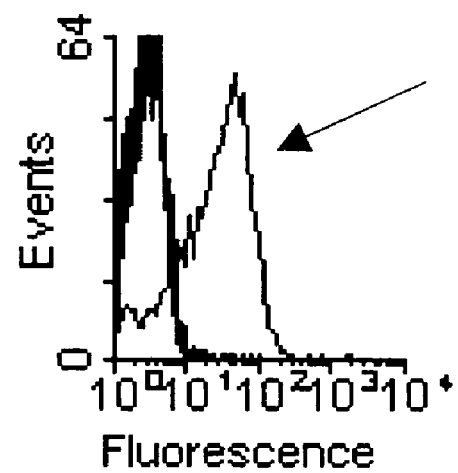
Figure 2C:
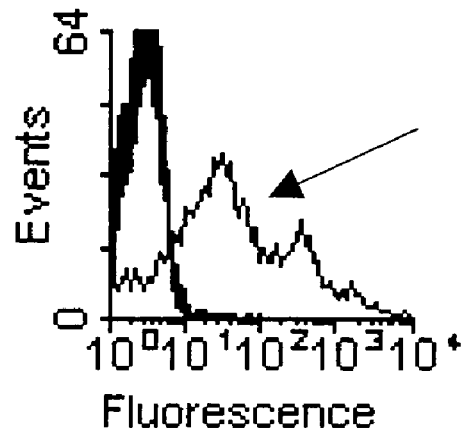

FIGS. 2A-2C are flow cytometry profiles of buffy coat from blood samples initially scored as: FIG. 2A: Weak; FIG. 2B: Strong; and FIG. 2C: Intermediate; by anti-Cpn FA stain of blood smear and/or by infection of J774A.1 monolayer cultures. Cpn negative results are shown in black and Cpn positive results are shown in grey and are labeled with an arrow (✓). Blood smears were made of samples tested by FC and immunostained using an anti-*chlamydia* primary antibody (BioMedia) and an FITC conjugated second antibody (Jackson ImmunoResearch). The guinea pig anti-*chlamydia* (from BioMedia) was detected with the Jackson FITC conjugated anti-*chlamydia* at 1:100 dilution. Using microscopic observations of immunostained blood smears, a specimen was designated as positive if it contained 3 clearly fluorescent cells/slide. These were designated as weakly positive. Depending on the number of fluorescent positive cells, additional smears of other samples were roughly divided into intermediate and strong positives. Not more than 8 positive cells (strong positive) per smear were found among the specimens initially examined and such specimens gave rise to the FC plots shown in FIGS. 2A-2C. This fact indicates that by assessing only 10,000 "events" (the minimum number the equipment used to generate these results will allow), clear distinctions between these three different specimens can be obtained. The equipment used to generate these results will count up to $1 \times 10^6$ events/sample, so sensitivity and discrimination can be readily and greatly increased. These findings demonstrate the potential analytical power of this technology for quantifying BC specimens for the number of *chlamydia* infected cells and defining specific infected cell subsets. Although not shown here, cells positive for *chlamydia* were also found to be positive for the leukocyte common antigen, CD45, which was detected using a monoclonal anti-CD45 (Sigma-Aldrich) with a PE fluorescent label.

For the negative (black) samples, 99% of the events were $\leq 10^1$ in terms of fluorescence and the mean fluorescence was $\leq 3.4$. In contrast, the strong positive shown in FIG. 2B—grey line, showed 63% of the total of 10,000 events were between $10^1$ and $10^2$ on the fluorescence scale and the mean fluorescence was 52.5. This is 15.4 times higher than the background mean of 3.4. For the intermediate positive (FIG. 2C), there were two peaks. The first peak between $\geq 10^{1-} \leq <10^2$ on the horizontal fluorescence scale (horizontal axis) contained 69% of the events with a fluorescence mean of 29.1 and a second smaller peak, based on fluorescence, between $\geq 10^{2-}$ and $\leq 10^3$ on the horizontal axis. It contained 22.03% of the events counted and had a fluorescence mean of 351.8. In addition, there was a minor peak at about $\geq 10^3$. It contained only 4% of the events counted, but the fluorescence mean was 2,100, indicating very significant labeling of cells in this otherwise minor peak.

These demonstrate that flow cytometric analysis is an effective screening method for Cp-containing cells in the PBC of infected patients without visible signs of chlamydial infection.

Example 2

Detection of Intracellular Pathogens

The following example illustrates a protocol for use in detecting *chlamydia* in a patient. The following protocol is strictly exemplary and not intended to be limiting in any way.

White Blood Cell Isolation:

1. 5 ml of blood is collected in EDTA or other anticoagulant solution and allowed to stand overnight in the cold. This allows the white blood cells to separate naturally from the underlying red blood cells (RBC) and overlying plasma.

2. White buffy coat layer (BC) is collected with a pipet or cannula and gently BC layer is expelled into phosphate buffered saline (PBS) pH ~7.0-7.2 and pelleted by gentle centrifugation (400×g). This PBS washing step is repeated 2 more times.

Immunostaining

Immunostaining is performed using standard protocols such as the one described below, or the one described below with minor modifications regarding antibody concentration, time and temperature for incubation. The protocol can also vary depending on whether (a) the detecting antibody is directly conjugated to a fluorophore such as fluorescein isothyocyanate (FITC) or phycoerythrin (PE) and/or (b) a secondary antibody such as anti-mouse or anti-rabbit, which is conjugated with a fluorophore, is used to detect binding of the *chlamydia* specific antibody. In either case, following incubation, ~2-3 ml of PBS is added to the tube containing cells and mixed. The cells are collected by gentle centrifugation as described above. This step is repeated to for a total of 3-4 washes. The precise number of cells immunostained may vary.

For immunostaining intracellular antigens, cells are fixed with 1% buffered paraformaldehyde (10 min at RT). It should be noted, however, that GLXA is clearly displayed on infected cell surfaces in addition to being retained within the intracellular inclusion. Paraformaldehyde fixation can be used for cells labeled by fluorochrome-conjugated antibodies to membrane antigens. It will stabilize the light scatter and labeling for up to a week in most instances, so a practitioner can be more flexible in scheduling cytometer time. It also inactivates most biohazardous agents. As relevant, in the case of intracellular vs. cell membrane displayed antigens, cells are permeabilized using 1% TRITON X 100 in addition to the 1% paraforrnaldehyde fixation.

1. 20 µl (approximately 1 µg) of specific monoclonal antibody, or 200 ul of an appropriate concentration of commercially available polyclonal antibody such as guinea pig anti-*chlamydia* (BioMedia @1:100 as determined by pre-titration), are added to a sample of BC cells (~1.5-2.0×10⁷—cell number determined by counting with a hemocytometer). Immunostaining of greater numbers of cells should use appropriately increased amounts of primary, and as/if relevant, secondary antibody.

2. The sample is mixed and incubated for 30-60 minutes at R.T.

3. The sample is rinsed with PBS multiple times as noted above and, as necessary, incubated with a conjugated secondary antibody using appropriate secondary antibody concentrations, and time and temperature parameters as determined by preliminary testing—generally 30-60 min at R.T.

4. Rinse 3-4 times by re-suspension in fresh PBS, followed by gentle centrifugation. When paraformaldehyde fixed, the samples can be stored at 4° C. prior to assessing by FC.

5. Samples are mixed in tube immediately before analysis to ensure cells are optimally dispersed cells, and passed through a nylon filter to exclude clumps which may not have been fully dispersed.

Isolation of Monocytes

If desired, the monocyte population of a sample can be obtained as follows: Add 5 ml of blood in anti-coagulant to a 15 ml centrifuge tube. Dilute the blood with 5-8 ml PBS+ azide and using a pipet or canula, underlay the blood/PBS sample with 2-5 ml FICOLL-HYPAQUE™ and use standard density centrifugation (FICOLL-HYPAQUE™, Pharmacia, Uppsala, Sweden). Remove the PBS/plasma upper layer and transfer the cells at the interface with the red cells to a fresh tube and rinse with PBS and carry out cell counts after re-suspension of the final cell pellet. This enriched population can then be stained for *chlamydia* as discussed above. Since *chlamydia* appear able to infect numerous cell types, certain flow cytometric screenings can examine the full array of white cells in a BC preparation. In addition, different subset populations of the total white cell population in a BC prep can be distinguished using commercially available monoclonal antibodies specific for subset surface markers such as CD4 (TH cells) or CD8-cytotoxic T cells (TC), and B cells (using antibody to immunoglobulin heavy and light chains).

Results

Specimens from diagnosed pediatric asthma patients and non asthma respiratory pediatric patients (blood and bronchial lavage-smear and culture) and blood samples from a pediatric health clinic practice were examined. The results are provided in Table 1 and Table 2, below. As indicated below, the number of smear and culture positives for bronchial alveolar lavage (BAL) are essentially the same as for blood.

TABLE 1

BAL Culture
P = 0.026
BAL Cult. * Asthma Vs Non-Asthma Crosstabulation

| | | | Asthma Vs Non-Asthma | | |
|---|---|---|---|---|---|
| | | | Asthma | Non-Asthma | Total |
| BAL Cult. | No | Count | 21 | 16 | 37 |
| | | % within BAL Cult. | 56.8% | 43.2% | 100.0% |
| | Yes | Count | 14 | 6 | 20 |
| | | % within BAL Cult. | 70.0% | 30.0% | 100.0% |
| Total | | Count | 35 | 22 | 57 |
| | | % within BAL Cult. | 61.4% | 38.6% | 100.0% |

TABLE 2

Blood Culture
P = 0.012
Blood Culture * Asthma Vs Non-Asthma Crosstabulation

| | | | Asthma Vs Non-Asthma | | |
|---|---|---|---|---|---|
| | | | Asthma | Non-Asthma | Total |
| Blood Cult. | No | Count | 20 | 15 | 35 |
| | | % within Blood Cult. | 57.1% | 42.9% | 100% |
| | Yes | Count | 15 | 7 | 22 |
| | | % within Blood Cult. | 68.2% | 31.8% | 100% |
| Total | | Count | 35 | 22 | 57 |
| | | % within Blood Cult. | 61.4% | 38.6% | 100% |

Preliminary Pediatric Data: Summary 57 total sequentially collected respiratory patient samples:
35 asthma & 22 non-asthma respiratory samples.
Average age: 8 yrs.
70% of BAL culture + were from children diagnosed with asthma.
68% of the blood culture + were from children diagnosed with asthma.
80% of the elevated anti-IF titers were from children diagnosed with asthma Respiratory Patient Diagnoses 54% pediatric patients diagnosed asthmatics.
46% non-asthma- Non asthma diagnoses included:
aspiration, gastro- esophageal reflux (GER) structural anomaly, recurrent bacterial pneumonia & cystic fibrosis.
Significance shown in crosstabulations was calculated using SPSS statistical program and Fisher's Exact Test.

Non-Respiratory Pediatric Blood Samples: Health Clinic 11.3% of 57 pediatric health clinic [HC], blood specimens collected during the same months were Cpn+ by smear or culture. Average age 6 yrs..

Example 3

Profiling of Cell Type Distribution of Cells Infected by *Chlamydia*, Using Confocal Microscopy and Flow Cytometry Analysis Immunostain of Blood Donor Smears Smears were prepared by placing approximately 20 ul of whole blood from EDTA tubes of blood donor samples on a clean glass slide, and using a second slide held at a 30-40° angle, were spread along the slide to complete the smear. Smears were allowed to dry, and were then fixed for 10 minutes using 70% cold methanol. Slides were incubated with a 1:50 dilution of a rabbit anti-*Chlamydia* serum 00MS78. After rinsing in 1×PBS, a 1:100 dilution of a FITC-conjugated goat anti-rabbit IgG (H+L) (Jackson Immuno Research Laboratories Inc, West Grove, Pa.) secondary antibody was added. Incubations with primary and secondary antibody solutions were allowed to occur for 1 hr at RT. After rinsing briefly in a beaker of PBS, coverslips were mounted using FLUOROMOUNT G™ (BioWhittaker, Walkersville, Md.), then sealed, examined and photographed using a Nikon Eclipse E600 epifluorescence microscope and a SPOT™ digital camera (Digital Instruments Inc.).

Monocyte, Eosinophil/Basophil, and Neutrophil Staining

Blood smears of fresh blood (FB) samples were prepared in triplicate using methods as described above, with the exception that gentle heat fixation was used instead of 70% methanol fixation. FB samples, available ≦7 days after collection, were used and a differential cell count was obtained using a standard Wright Giemsa staining protocol provided by the by manufacturer (ACCRA by Fisher Scientific, Middletown, Va.) to assess WBC fragility, death, or loss during preparation. The FB smears were dually immunostained by incubating the smears with the polyclonal rabbit anti-*Chlamydia* serum and either mouse monoclonal anti-Human CD 14 (Sigma, Saint Louis, Mo.), PE-conjugated mouse monoclonal anti-Human CDw125 or mouse monoclonal anti-Human CD 16b. All dilutions were made in PBS. The final antibody concentrations were as follows: rabbit anti-*Chlamydia* polyclonal 1:100 and 20 ul CD 14 per $10^6$ cells, 5 ul of CDw125 per $10^6$ cells, and 2 ul of CD16b per $10^6$ cells.

These were co-incubated on individual slides for 1 hour at RT. After a brief rinse in a beaker with PBS, all samples were incubated with fluor-labeled secondary antibody. To identify CD 14 or CD16b infected cells, a 1:100 dilution of FITC-conjugated goat anti-mouse IgG (H+L) was added to the slides concurrently with the TRITC Goat anti-Rabbit IgG (H+L) antibody. The anti-CD125w was directly conjugated with phycoerythrin (PE). Therefore, the rabbit anti-*chlamydia* antibody binding was identified with a 1:100 dilution of FITC-conjugated Goat anti-Rabbit IgG (H+L). Unless otherwise specified, all incubations were carried for 1 hour at RT. Following incubation and several rinses with PBS, samples were coverslipped using Flouro-G as noted above. The immuno-labeled cells were observed by fluorescence microscopy using the Zeiss LSM 510 Meta Confocal System.

Flow Cytometry of Fresh Blood WBCs: Dual Immunostain for Eosinophils and Neutrophils BC material was removed from EDTA blood tubes of FB samples and placed in microfuge tubes. The cells were washed twice in sterile 1×PBS and collected by 15 second centrifugation at 12,400 rpm. Cells were assessed for viability by Trypan Blue exclusion and counted with hemocytometer. At RT, cells were then fixed with 1% paraformaldehyde and permeabilized for 10 minutes with 1% TRITON X-100™ (Aldrich Chemical Company, Inc., Milwaukee, Wis.). After rinsing twice as described above, BC cells were incubated for 1 hour with a polyclonal Guinea pig anti-*Chlamydia* primary antibody (Biomeda Corp. Foster City, Calif.) and either mouse monoclonal PE conjugated anti-Human CDw125 or mouse monoclonal anti-Human CD16b. BC ells were washed 3× as above, then incubated with either 1:100 dilution of FITC conjugated F(ab')2 Donkey anti-Guinea pig (H+L), or a 1:100 dilution of R-PE-conjugated F(ab')2 Donkey anti-Guinea pig IgG (H+L) and 1:100 dilution FITC-conjugated Rabbit anti-mouse IgG (H+L) (Jackson Immuno Research Laboratories Inc, West Grove, Pa.). Samples were then washed 3× as above, passed through a nylon mesh filter to mono-disperse cells (Lab-Line Instruments Inc, Melrose Park, Ill.). This dispersed sample was counted again by hemocytometer and diluted to 1×106 cells/ml as necessary and analyzed by flow cytometry. All fixation, permeabilization, and incubations with antibody were carried out at RT.

Flow Cytometry of WBC Serial Dilution

Buffy coats, and separately RBC, from blood samples were washed and prepared as above, and then the buffy coat-derived WBC and RBC pooled separately. WBC and RBC pools were stained separately with a polyclonal Guinea pig anti-*Chlamydia* primary antibody (Biomeda Corp. Foster City, Calif.) and a 1:100 dilution of R-PE-conjugated F(ab')₂ Donkey anti-Guinea pig IgG (H+L). Samples were then washed 3× as above and passed through a nylon mesh filter to mono-disperse the cells (Lab-Line Instruments Inc, Melrose Park, Ill.). Cells in pools were counted by hemocytometer and WBCs were added into separate tubes as follows: 100% (50,000 cells), 90%, 80%, 70%, 60%, 50%, 40%, 30%, 20%, 10%, 5%, 2%, 1%, 0.5%, and 0%. As necessary, RBCs were added to each tube to obtain 50,000 total cells/sample. A 10,000 cell sample of each of the dilutions was then used for flow cytometry analysis.

Results

Figure 3A:
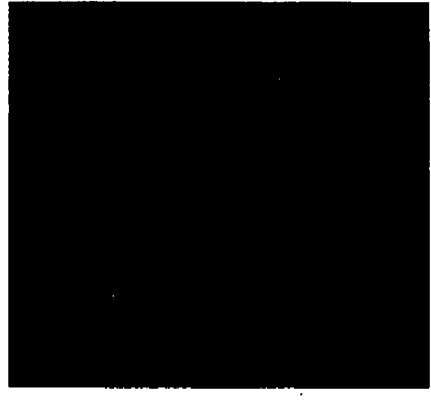
FIGS. 3A-3C are photomicrographs illustrating immunofluorescence staining for chlamydial antigen in a blood smear sample containing *chlamydia* infected cells.
Figure 3B:
Figure 3C:

Blood smears were prepared by standard methods, then stained with a rabbit anti-*chlamydia* antibody. Antibody binding was detected with a FITC conjugated secondary antibody. FIGS. 3A and 3B show *Chlamydia* infection-positive smears in which characteristic chlamydial inclusions are immunostained (FITC, green). FIG. 3C is a smear that was negative for characteristic chlamydial inclusions as determined using anti-*chlamydia* immunostaining.

Figure 4A:
FIGS. 4A and 4B are photomicrographs illustrating immunofluorescence staining for a chlamydial antigen in cultures of peripheral blood cells co-cultured with a J774A.1 host cell monlayer.
Figure 4B:

BC samples from peripheral blood circulation were cultured in vitro to determine whether *Chlamydia* present in blood cells was capable of infecting other cells. FIG. 4A shows a specimen after 96 h of culture on J774A.1 host cell monolayers, which demonstratesthe presence and infectious nature of *Chlamydia* carried within the WBC of a normal blood donor sample. FIG. 4B shows the same type of monolayer after 96 h culture with a *chlamydia*-negative WBC sample. Thus, chlamydial inclusions visualized in WBC of the blood were clearly shown to include infectious chlamydial units.

Figure 5:
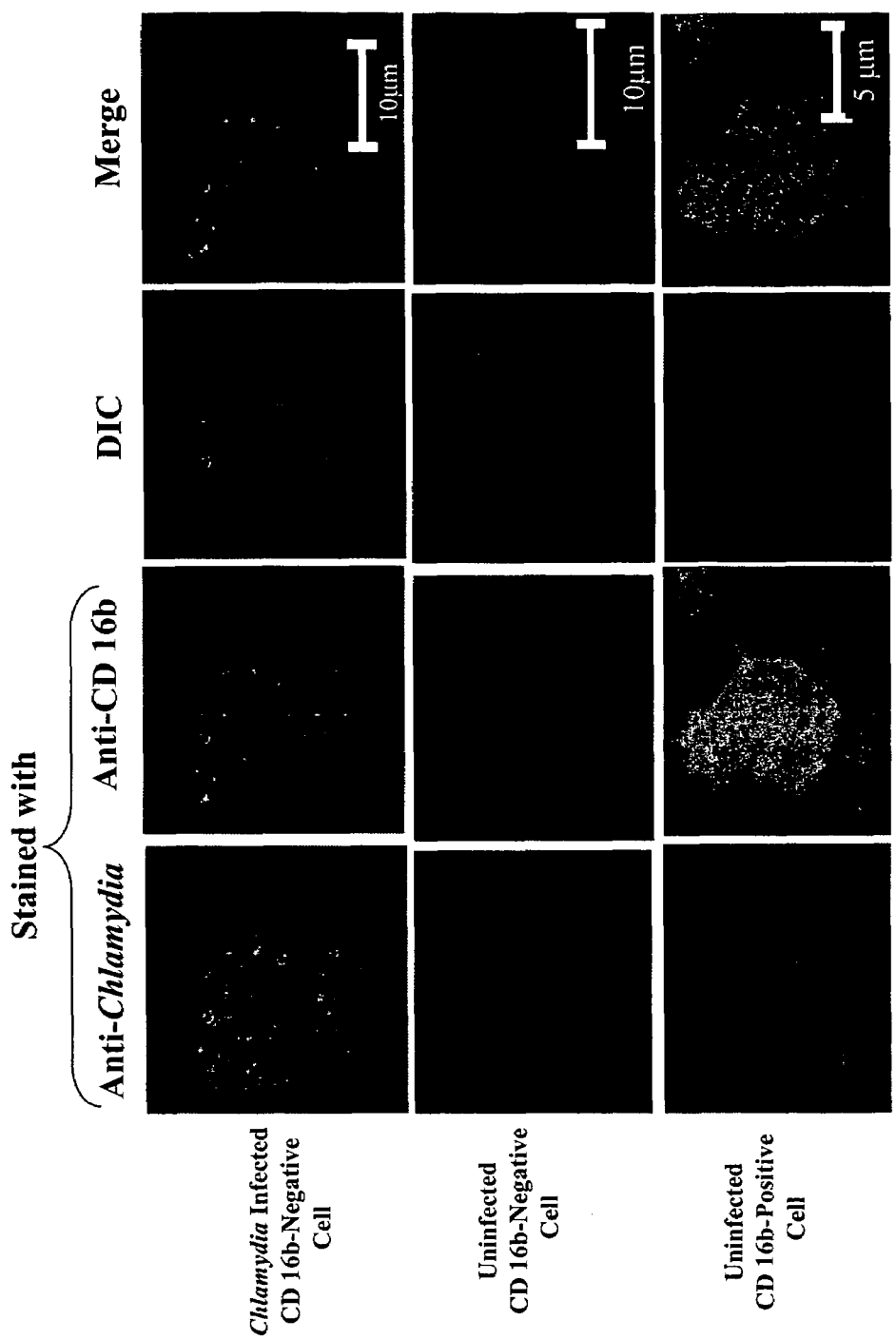
FIG. 5 is a set of photomicrographs illustrating differential immunostaining of *chlamydia*-infected and uninfected CD16b positive and CD16b negative cells. Cells were stained with anti-*chlamydia* and anti-CD16b antibodies. Top row: *chlamydia* infected CD16b negative cells. Middle row: uninfected CD16b-negative cells. Bottom row: uninfected CD16b-positive cells.

In order to detect the presence of *chlamydia* in specific cell types (e.g., white blood cell types), dual imrnunofluorescence staining was performed to detect both *chlamydia* and a cell-type specific antigen. Importantly, as shown in FIG. 5 (top row), anti-*chlamydia* immunofluorescence (red) produces little or no background fluorescence in the detection of anti-CD 16b immunofluorescence (green). Conversely, as seen in the bottom row of FIG. 5, anti-CD 16b immunofluorescence causes no or negligible background in the detection of anti-*chlamydia* fluorescence. Also, non-specific background fluorescence is low or absent as seen in the middle row of FIG. 5.

Figure 6:
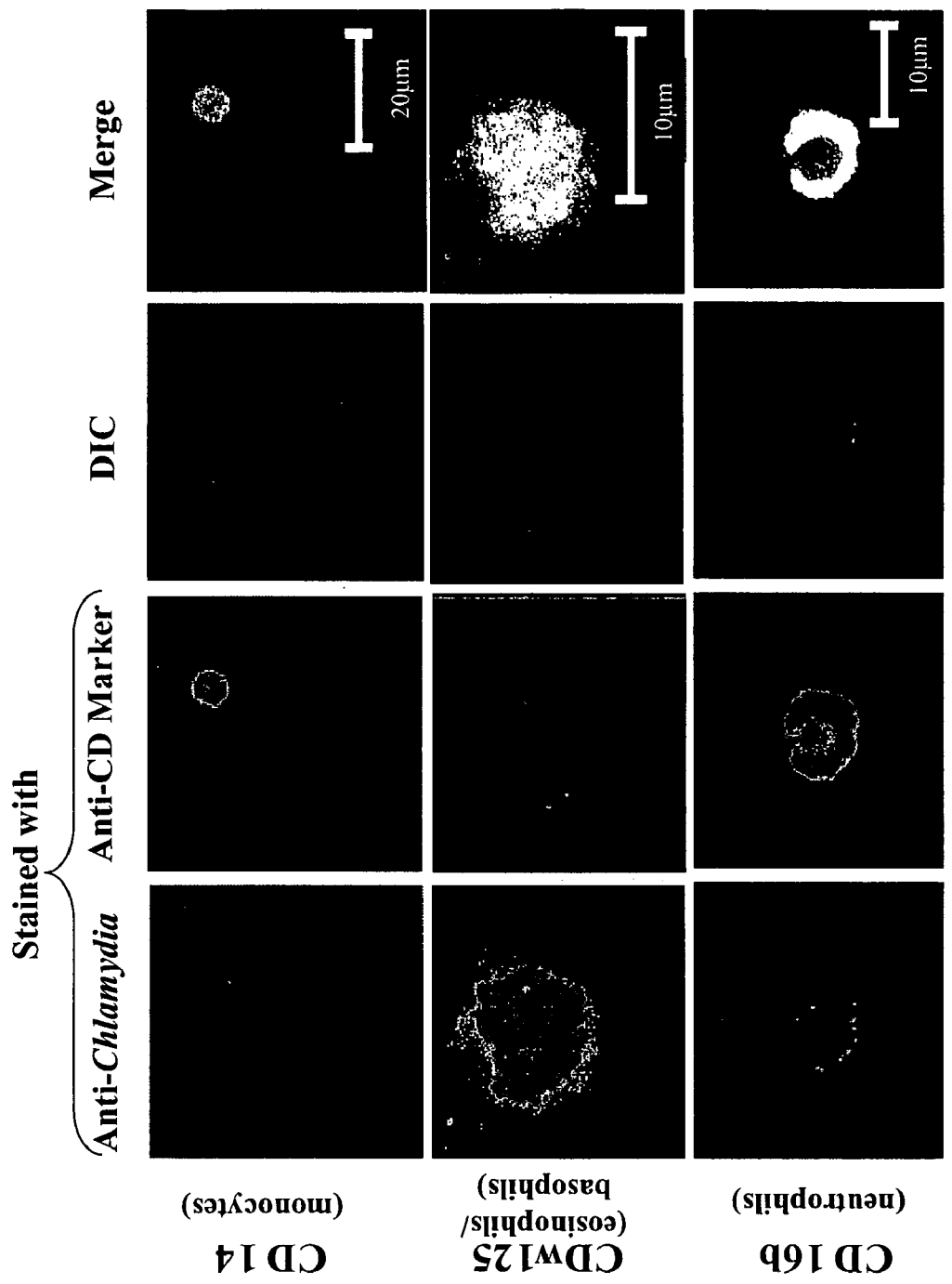
FIG. 6 is a series of photomicrographs of confocal double immunofluorescence staining for chlamydial antigens and a cell type-specific cluster of differentiation (CD) antigen. The first column shows staining with an anti-*chlamydia* antibody (PE staining (red) in top and bottom rows; FITC staining (green) in middle row). The second column shows staining with an anti-CD marker antibody. (FITC staining (green) in top and bottom rows; PE staining (red) in middle row). Expression of CD marker antigens is cell-type specific (cell types noted in parentheses). The third column is a differential interference contrast (DIC) bright field image that shows all cells present in the field. The fourth column shows a merged image of the preceding images observed in columns 1-3. Cells that express that are positive for both chlamydial antigens and the CD marker being stained are yellow in the merged image. Cells that express only one of the antigens being stained are only one color (e.g., the cell in the bottom left corner of column 4, row 1).

A range of white blood cell types in the peripheral blood circulation were found to be infected by *chlamydia* as shown in FIG. 6, including monocytes (top row), eosinophils/basophils (middle row (note that in this row, *chlamydia* staining is in green)), and neutrophils (bottom row). Dual immunofluorescence staining for *chlamydia* and a cell-type specific marker was observed clearly in merged images of red-staining (anti-*chlamydia* except for the middle row) and green staining (anti-cell type marker except for the middle row) to give yellow staining, as shown at the end of each row. In the case of dual immunofluorescence staining for *chlamydia* and CD 14 (top row), both cells visible in the field (see differential interference contrast (DIC) image) are positive for anti-*chlamydia* immunofluorescence, but only one of the cells was positive for anti CD 14 immunofluorescence (note merged image), which again demonstrated the specificity of the dual immunofluorescence technique.

Figure 7:
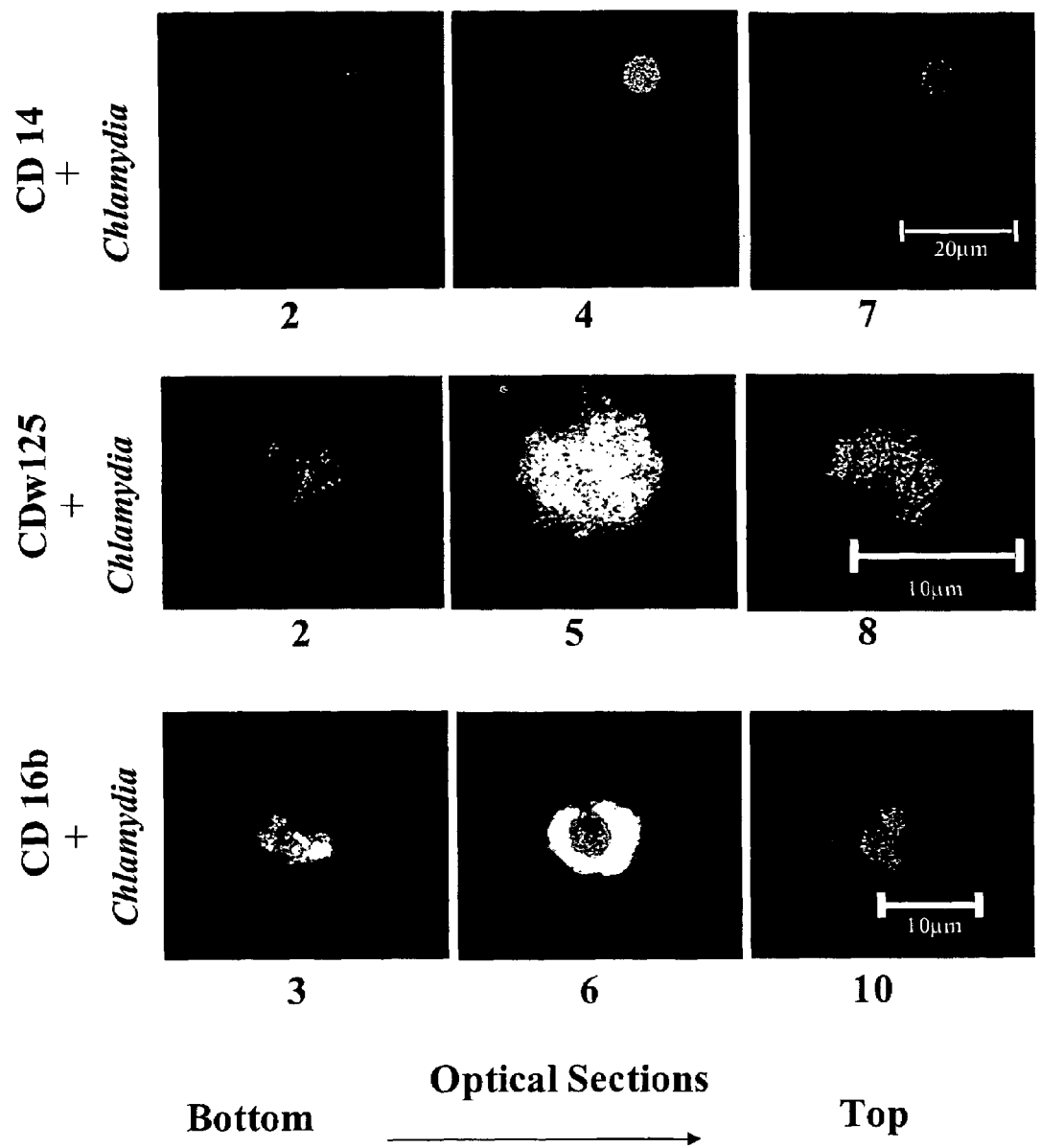
FIG. 7 is a series of confocal optical section photomicrographs of double immunofluorescence staining for chlamydial antigens and a cell type-specific CD antigen (merged images), which proceed from the bottom of the cell and proceed towards the top of the cell(s). Anti-chlamydial staining is red and anti-CD marker staining is green, thus areas of colocalization of the stained antigens appears as yellow in each image. High resolution confocal optical sectioning through the cells (sections numbered from bottom to top; ordered from left to right) allows subcellular localization of chlamydial antigens and chlamydial inclusions in specific cell types.

The subcellular localization of chlamydial antigens and chlamydial inclusions in specific cell types was observed by confocal microscopy imaging. Confocal images of dual immunofluroscence anti-*chlamydia* and anti-CD marker staining are shown in FIG. 7. Each row of FIG. 7 shows a series of merged images of confocal optical sections of anti-*chlamydia* and anti-CD marker immunofluorescence staining. The numbers below each image refer to the section number in the series starting from the bottom surface of the cell(s) and proceeding upwards through the top of the cell(s).

Figure 8:
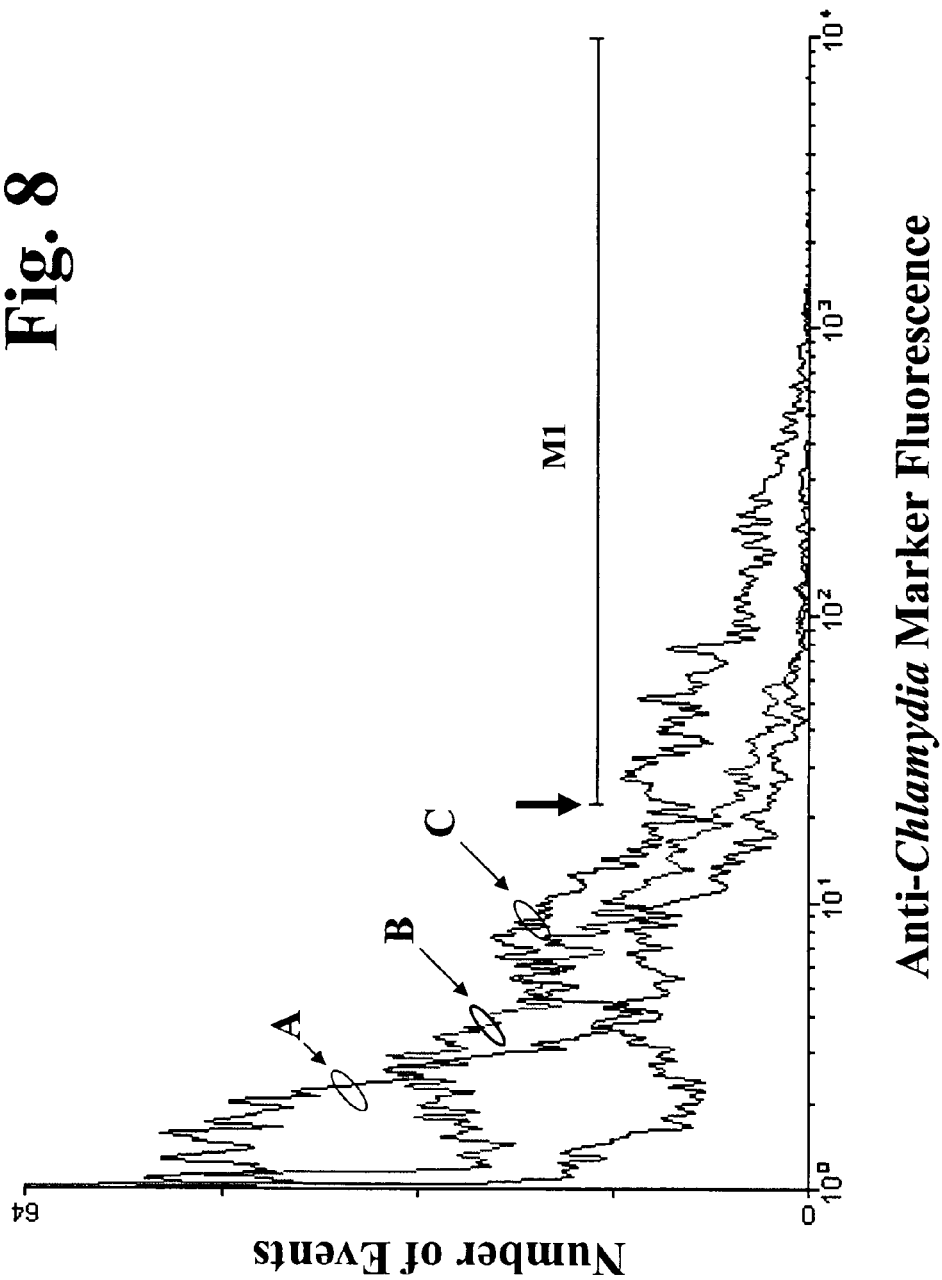
FIG. 8 is a set of frequency distribution histograms of buffy coat-derived cell populations. The cells were stained for chlamydial antigens and an eosinophil/basophil-specific marker (CDw125) and analyzed using flow cytometry. The histograms show a distribution of cells (or "events") based on anti-*chlamydia* immunofluorescence. The histogram labeled "A" depicts an uninfected cell population stained solely with a secondary antibody (as a fluorescence background control). The hjistogram labeled "B" depicts a known uninfected cell population stained with anti-*chlamydia* and anti-CDw125 primary antibodies and detected with a fluorophore-conjugated secondary antibody. The histogram labeled "C" depicts a population of cells known to include some *Chlamydia*-infected cells and stained with the same primary antibodies used for "B." "M1" represents the threshold fluorescence criterion used to judge a cell as being positive for the marker.

The data above demonstrate that *chlamydia* infects a variety of white blood cell types and can be localized subcellularly within those cell types. Dual immunofluorescence flow cytometry was used to quantitatively assess the distribution of *chlamydia* infected cells within particular white blood cell type populations. The flow cytometer measures fluorescence intensity in two channels simultaneously (e.g., anti-*chlamydia* immunofluorescence in the red channel and anti-CDw125 immunofluorescence in the green channel) and, therefore, each cell can be classified as infected or uninfected and cell type marker-positive or negative, according to the respective immunofluorescence intensities for that cell. In FIG. 8, the anti-*chlamydia* immunofluorescence intensity histograms are plotted for three populations of cells (labeled A, B, and C). The "A" histogram shows the distribution of immunofluorescence intensities that were detected in a population of uninfected cells stained only with a fluorophore-conjugated secondary antibody. The "A" histogram data were used to determine the non-specific background fluorescence associated with a secondary antibody. The "B" histogram shows the distribution of immunofluorescence intensities that were detected in a population of uninfected cells. The "C" histogram shows the distribution of immunofluorescence intensities that were detected in a population of cells known to include some *chlamydia* infected cells. Cells exhibiting an anti-*chlamydia* immunofluorescence intensity approximately equal to or greater than 20 (indicated by arrow and M1 line) were considered to be infected with *chlamydia*. Only 2% of the B histogram population (uninfected population) reached this threshold of immunofluorescence intensity, which means that 2% of the detected events equal to or above this fluorescence intensity threshold were due to background immunostaining.

Figure 9:
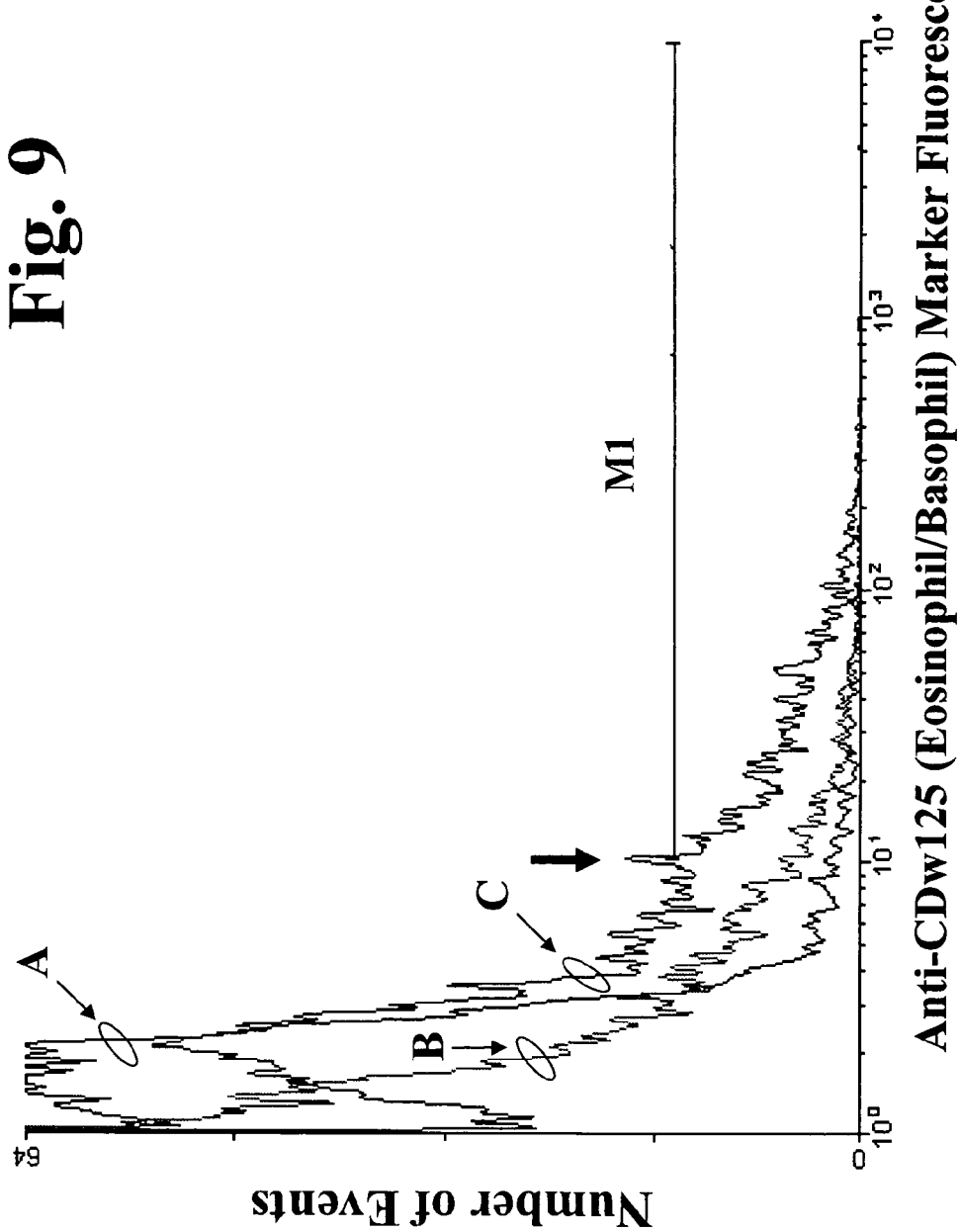
FIG. 9 is a set of frequency distribution histograms of buffy coat-derived cell populations. The cells were stained for chlamydial antigens and an eosinophil/basophil-specific marker (CDw125) and analyzed using flow cytometry. The histograms show distribution of cells (or "events") based on anti-CDw125 immunofluorescence. The histogram labeled "A" depicts an uninfected cell population stained only with a secondary antibody (as a fluorescence background control). The histogram labeled "B" depicts an uninfected cell population. The histogram labeled "C" depicts a cell population that includes some cells that are positive for anti-*chlamydia* immunofluorescence.

In FIG. 9, the distribution of anti-CDw125 immunofluorescence intensities. are shown for the populations of cells (B and C) shown in FIG. 8. A threshold fluorescence intensity for CDw125 detection positivity was defined as equal to or greater than 20. Interestingly, the relative proportion of CDw125-positive cells (eosinophils/basophils) was different in the uninfected (A) population versus the (B) population that includes a subpopulation of *chlamydia* infected cells.

Figure 10:
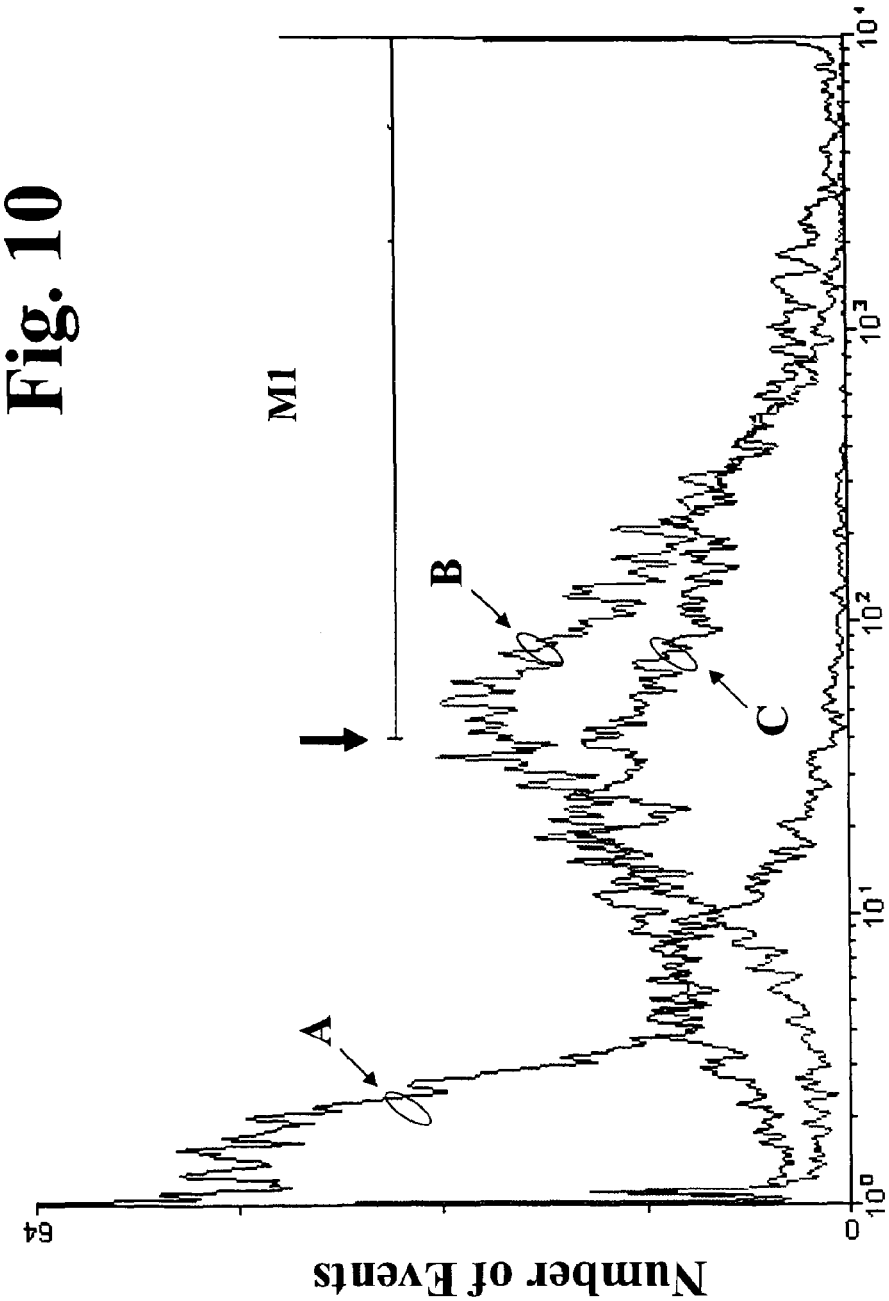
FIG. 10 is a set of frequency distribution histograms of buffy coat-derived cell populations. The cells were stained for chlamydial antigens and a neutrophil-specific marker (CD16b) and analyzed using flow cytometry. The histograms show distribution of cells (or "events") based on anti-CD 16b immunofluorescence. The histogram labeled "A" depicts an uninfected cell population stained only with a secondary antibody (as a fluorescence background control). The histogram labeled "B" depicts CD 16b immunofluorescence in an uninfected cell population. The histogram labeled "C" depicts CD 16b immunofluorescence in a cell population that includes cells that are positive for anti-*chlamydia* immunofluorescence.

In FIG. 10, the same type of analysis was performed, except that the cell type marker detected was CD 16b, which is specific to neutrophils.

These data provided above establish that dual immunofluorescence flow cytometry can be used to detect both chlamydial antigens and the specific cell types expressing them within a given cell population.

To confirm the sensitivity and accuracy of flow cytometry, a population of infected white blood cells was serially diluted with red blood cells and analyzed. The results are provided in FIG. 11, which illustrates graphically that the number of detected cells in the sample population was linearly related to the dilution of the infected cells with uninfected cells. The vertical axis indicates the total number of white blood cells in the corresponding 10,000 cell sample that was analyzed (e.g. a 50% dilution of white blood cells with red blood cells corresponds to 5,000 cells on the vertical axis). The horizontal axis indicates the number of infected cells detected in the sample. As would be expected the number of detected infected cells is linearly related to the dilution as shown in FIG. 11. As few as three infected cells in 10,000 could be detected by the technique. These results further demonstrate that flow cytometry is both precise and sensitive in detecting *chlamydia* infected cells in a large population of uninfected cells.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method of profiling distribution of *Chlamydia*-infected cell types in a biological sample of a subject, the method comprising:
   (a) obtaining a biological sample from a subject;
   (b) contacting the biological sample with a first antibody that binds specifically to a chlamydial antigen present in or on the surface of a *Chlamydia*-infected cell and with a second antibody that binds specifically to a cell type-specific antigen;
   (c) analyzing the biological sample from step (b) using flow cytometry to detect and count a cell in the sample with the first antibody bound thereto, wherein the cell with the bound first antibody is counted as a *Chlamydia*-infected cell; and
   detecting the cell in the sample from step (c) that is bound to the second antibody, wherein the cell in the sample bound to both the first antibody and the second antibody is counted as a *Chlamydia*-infected cell that expresses the cell type-specific antigen.

2. The method of 1, wherein the cell type-specific antigen is expressed by a cell selected from the group consisting of a basophil, eosinophil, neutrophil, dendritic cell, mast cell, and monocyte.

3. The method of 2, wherein the cell type-specific antigen is expressed by the basophil.

4. The method of 2, wherein the cell type-specific antigen is expressed by the eosinophil.

5. The method of 2, wherein the cell type-specific antigen is expressed by the neutrophil.

6. The method of 2, wherein the cell type-specific antigen is expressed by the monocyte.

7. The method of 1, wherein the cell type-specific antigen is CD16b.

8. The method of 1, wherein the cell type-specific antigen is CDw125.

9. The method of 1, wherein the cell type-specific antigen is CD14.

10. The method of 1, wherein the first antibody or the second antibody, or both, is labeled by at least one fluorophore.

11. The method of 10, wherein the fluorophore is selected from the group consisting of 7-amino-4-methylcoumarin-3-acetic acid (AMCA), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin, 3-carboxylic acid, 6-fluorescein 5 (and-6)-carboxamidohexanoic acid, N-(4,4-difluoro-5,7-dimethyl-4-bora-3a,4a diaza-3-indacenepropionic acid, eosin-5-isothiocyanate, erythrosin-5-isothiocyanate, phycoerythrin (B-, R-, or cyanine-), and allophycocyanin.

* * * * *

UNITED STATES PATENT AND TRADEMARK OFFICE
CERTIFICATE OF CORRECTION

PATENT NO. : 7,455,985 B2 Page 1 of 1
APPLICATION NO. : 11/107293
DATED : November 25, 2008
INVENTOR(S) : Elizabeth S. Stuart and Lloyd H. Semprevivo It is certified that error appears in the above-identified patent and that said Letters Patent is hereby corrected as shown below:

Col. 18, line 23, delete "1," and insert -- claim 1, --.

Col. 18, line 27, delete "2," and insert -- claim 2, --.

Col. 18, line 29, delete "2," and insert -- claim 2, --.

Col. 18, line 31, delete "2," and insert -- claim 2, --.

Col. 18, line 33, delete "2," and insert -- claim 2, --.

Col. 18, line 35, delete "1," and insert -- claim 1, --.

Col. 18, line 37, delete "1," and insert -- claim 1, --.

Col. 18, line 39, delete "1," and insert -- claim 1, --.

Col. 18, line 41, delete "1," and insert -- claim 1, --.

Col. 18, line 44, delete "10," and insert -- claim 10, --.

Col. 18, line 51, delete "5 (and-" and insert -- 5-(and- --.

Signed and Sealed this

Ninth Day of June, 2009

JOHN DOLL
*Acting Director of the United States Patent and Trademark Office*